(12) United States Patent
Schuetzle et al.

(10) Patent No.: US 12,098,111 B2
(45) Date of Patent: *Sep. 24, 2024

(54) PROCESS FOR CAPTURE OF CARBON DIOXIDE FROM AIR AND THE DIRECT CONVERSION OF CARBON DIOXIDE INTO FUELS AND CHEMICALS

(71) Applicant: INFINIUM TECHNOLOGY, LLC, Sacramento, CA (US)

(72) Inventors: Robert Schuetzle, Sacramento, CA (US); Dennis Schuetzle, Grass Valley, CA (US); Harold Wright, Menomonee Falls, WI (US); Orion Hanbury, Sacramento, CA (US); Matthew Caldwell, West Sacramento, CA (US); Ramer Rodriguez, Sacramento, CA (US)

(73) Assignee: Infinium Technology, LLC, Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/803,834

(22) Filed: Dec. 15, 2022

(65) Prior Publication Data

US 2023/0373882 A1  Nov. 23, 2023

Related U.S. Application Data

(63) Continuation of application No. 17/300,259, filed on May 3, 2021, now Pat. No. 11,560,343.

(Continued)

(51) Int. Cl.
*C07C 1/04*   (2006.01)
*B01J 20/22*  (2006.01)
(Continued)

(52) U.S. Cl.
CPC ............. *C07C 1/0485* (2013.01); *B01J 20/22* (2013.01); *B01J 20/3425* (2013.01);
(Continued)

(58) Field of Classification Search
CPC . C07C 1/0485; C10G 2/32; C01B 2203/0244; C01B 2203/0233; C01B 32/40; C01B 3/40; C25B 1/04; C25B 15/081
See application file for complete search history.

(56) References Cited

U.S. PATENT DOCUMENTS 7,485,767 B2   2/2009  Lattner et al.
8,168,143 B2   5/2012  Severinsky
(Continued)

FOREIGN PATENT DOCUMENTS

CN   102198360 A   9/2011
JP   H03193112 A   8/1991
(Continued)

OTHER PUBLICATIONS

Albrecht, F., A standardized methodology for the techno-economic evaluation of alternative fuels—A case study. Fuel 194 (2017) 511-526.

(Continued)

*Primary Examiner* — Jafar F Parsa
(74) *Attorney, Agent, or Firm* — McKinney Law Group APC; Jeffrey A. McKinney

(57) ABSTRACT

The invention relates to a process, catalysts, materials for conversion of renewable electricity, air, and water to low or zero carbon fuels and chemicals by the direct capture of carbon dioxide from the atmosphere and the conversion of the carbon dioxide to fuels and chemicals using hydrogen produced by the electrolysis of water.

12 Claims, 6 Drawing Sheets

Related U.S. Application Data

(60) Provisional application No. 63/101,558, filed on May 4, 2020.

(51) Int. Cl.
  *B01J 20/34* (2006.01)
  *C01B 3/40* (2006.01)
  *C01B 32/40* (2017.01)
  *C25B 1/04* (2021.01)
  *C25B 15/08* (2006.01)

(52) U.S. Cl.
  CPC ............ *B01J 20/3441* (2013.01); *C01B 3/40* (2013.01); *C01B 32/40* (2017.08); *C25B 1/04* (2013.01); *C25B 15/081* (2021.01); *C01B 2203/0233* (2013.01); *C01B 2203/0244* (2013.01)

(56) References Cited

U.S. PATENT DOCUMENTS

| | | |
|---|---|---|
| 8,198,338 B2 | 6/2012 | Shulenberger et al. |
| 8,557,218 B2 | 10/2013 | Sundaram et al. |
| 10,396,388 B2 | 8/2019 | Bosmann et al. |
| 11,649,164 B2 | 5/2023 | Mortensen |
| 11,655,421 B2 | 5/2023 | Heidel et al. |
| 2007/0244208 A1 | 10/2007 | Shulenberger et al. |
| 2009/0012188 A1 | 1/2009 | Rojey et al. |
| 2010/0137457 A1 | 6/2010 | Kaplan |
| 2010/0298131 A1 | 11/2010 | Ni et al. |
| 2012/0201717 A1 | 8/2012 | Singh et al. |
| 2016/0199810 A1 | 7/2016 | Goeppert et al. |
| 2019/0292048 A1 | 9/2019 | Kusche et al. |
| 2021/0113980 A1 | 4/2021 | Van Der Ploeg |

FOREIGN PATENT DOCUMENTS

| | | |
|---|---|---|
| JP | 2010235736 A | 10/2010 |
| WO | 03035590 A1 | 5/2003 |
| WO | 2008153826 A2 | 1/2008 |

OTHER PUBLICATIONS

Kibby, C. Chevron's gas conversion catalysis-hybrid catalysts for wax-free Fischer-Tropsch synthesis, Catalysis Today 215 (2013) 131-141.

Diamond, Alan, Office Action in United States Ex Parte Reexamination for U.S. Pat. No. 11,560,343, dated Jul. 11. 2024, 31 pages.

PROCESS FOR CAPTURE OF CARBON DIOXIDE FROM AIR AND THE DIRECT CONVERSION OF CARBON DIOXIDE INTO FUELS AND CHEMICALS

This application is a continuation of U.S. application Ser. No. 17/300,259, filed on May 3, 2021, which claims priority benefit of U.S. Provisional Patent Application No. 63/101,558, filed May 4, 2020. The entire content of these applications is hereby incorporated by reference herein in its entirety.

FIELD OF INVENTION

The invention relates to a process, catalysts, materials for conversion of renewable electricity, air, and water to low or zero carbon fuels and chemicals by the direct capture of carbon dioxide from the atmosphere and the conversion of the carbon dioxide to fuels and chemicals using hydrogen produced by the electrolysis of water.

BACKGROUND OF INVENTION

Carbon dioxide is produced by many industrial and biological processes. Carbon dioxide is usually discharged into the atmosphere and global carbon dioxide levels in the atmosphere have been increasing since the start of the industrial revolution. Carbon dioxide has been identified as a significant greenhouse gas that is responsible for global climate change. Reduction of carbon dioxide at the source of generation has been especially difficult and has not been generally successful. Carbon dioxide in the atmosphere continues to increase. A more preferred method to deal with carbon dioxide is to efficiently capture the carbon dioxide from ambient air and convert it into useful products such as fuels (e.g. diesel fuel, kerosene, jet fuel, gasoline or gasoline blendstocks, or other fuels) and chemicals (methanol, ammonia, solvents, waxes, olefins, or other chemicals) that can displace fuels and chemicals produced from fossil sources such as petroleum and natural gas and therefore lower the total net emissions of carbon dioxide into the atmosphere. This is what is meant by low carbon, ultra-low carbon, or zero carbon fuels and chemicals.

Carbon dioxide can be obtained from several sources. Industrial manufacturing plants that produce ammonia for fertilizer from natural gas or coal produce large amounts of carbon dioxide. Ethanol plants that convert corn or wheat into ethanol produce large amounts of carbon dioxide. Power plants that generate electricity from natural gas or coal produce large amounts of carbon dioxide. Natural gas deposits can also have large quantities of carbon dioxide so that natural gas processing plants in certain locations must deal with significant amounts of carbon dioxide. Capturing $CO_2$ for utilization often involves separating the carbon dioxide from a flue gas stream or another stream where the carbon dioxide is not the major component. An alkylamine is used to remove the carbon dioxide from the flue gas steam. Alkylamines used in the process include monoethanolamine, diethanolamine, methydiethanolamine, disopropylamine, aminoethoxyethnol, or combinations thereof. Metal Organic Framework (MOF) materials have also been used as a means of separating carbon dioxide from a dilute stream using chemisorption or physisorption to capture the carbon dioxide from the stream. Other methods to get concentrated carbon dioxide include chemical looping combustion where a circulating metal oxide material captures the carbon dioxide produced during the combustion process.

Carbon dioxide can also be captured from the atmosphere in what is called direct air capture (DAC) of carbon dioxide. The challenges of capturing carbon dioxide from the air are different than from flue gas or other sources as the carbon dioxide concentration in air is quite low at approximately 415 ppm. The liquid alkylamines do not work well at these low concentrations as the losses of amine are often too high. MOF compounds based on physical absorption of carbon dioxide typically have too low an uptake of carbon dioxide. A publication, Sanz-Perez, et al, "*Direct Capture of $CO_2$ from Ambient Air*", Chem. Rev. 2016, 116, 11840-11876 details the historical development of the Direct Air Capture of $CO_2$. Numerous materials have been tried to capture carbon dioxide from dilute air streams.

Two major types of materials and processes have developed as the most promising over the last decade. The first promising set of materials and processes is the use of Amine-tethered solid sorbents. This involves the $CO_2$ capturing capacity of amines (like the liquid amines mentioned above) but with those types of materials chemically tethered to solids. Unlike the metal oxide based chemisorbents described above, supported amine absorbents operate at near ambient conditions and can ideally be regenerated by mild temperature swings. Choi et al, "*Application of Amine-Tethered Solid Sorbents for Direct $CO_2$ Capture from Ambient Air*", Environmental Science & Technology, 2011, 45, 2420-2427 describes these materials in detail. These chemisorbents however require temperature swings to release the carbon dioxide as well as an inert gas to sweep away the carbon dioxide. In the laboratory, nitrogen or argon or other inert gases are used. However, commercially, the separation of the inert gas from the carbon dioxide becomes a problem almost as significant as the initial capture of the carbon dioxide. To overcome the inert gas problem, for certain of these supported adsorbents, it has been shown that steam can be used to release the carbon dioxide and regenerate the adsorbent. See Wen Li, et. Al "*Steam Stripping for Regeneration of Supported Amine-Based $CO_2$ Adsorbents*", ChemSusChem 2010, 3, 899-903. Technology developed by Global Thermostat as described in U.S. Pat. No. 9,555,365 falls into this general category of approaches for DAC.

The second materials and processes are the use of aqueous metal hydroxides to react with the $CO_2$ in the air to produce a metal carbonate which is then calcined to release the captured $CO_2$ and recreate the metal hydroxide. This cycle can be done in a continuous series of chemical reactors. This is the technology being scaled up by Carbon Engineering. Their process is discussed in detail in Keith et al, "*A Process for the Capture of $CO_2$ from the Atmosphere*", Joule 2, 1573-1594, Aug. 15, 2018. The resultant carbon dioxide from their process is cooled from 900° C. and compressed to over 100 atmospheres to either be geologically sequestered or to go to a $CO_2$ pipeline. Renewable sources of Hydrogen ($H_2$) can be produced from water via electrolysis.

$$H_2O = H_2 + \tfrac{1}{2}O_2$$

This reaction uses electricity to split water into hydrogen and oxygen. Electrolyzers consist of an anode and a cathode separated by an electrolyte. Different electrolyzers function in slightly different ways, mainly due to the different type of electrolyte material involved.

However, each electrolysis technology has a theoretical minimum electrical energy input of 39.4 kWh/kg$H_2$ (HHV of hydrogen) if water is fed at ambient pressure and temperature to the system and all energy input is provided in the form of electricity. The required electrical energy input may be reduced below 39.4 kWh/kg$H_2$ if suitable heat energy is provided to the system. High temperature electrolysis, such as PEM steam electrolysis and particularly solid oxide electrolysis could have lower operating costs if the electrolyzer were co-located with a low cost or waste heat source, than if all the energy were provided through electricity. (*Study on development of water electrolysis in the EU Final Report, E4tech Sàri with Element Energy Ltd for the Fuel Cells and Hydrogen Joint Undertaking*, February 2014). Given the high energy required for electrolysis, placement of a zero carbon fuels and chemical facility as envisioned by this invention will have to be located at or near a location with inexpensive renewable electricity.

Besides electrolysis, significant current research is examining ways to split water into hydrogen and oxygen using light energy and a photocatalyst. (Acar et al, *Int. J. Energy Res.* 2016; 40:1449-1473).

Recent developments in Liquid Organic Hydrogen Carriers (LOHC's) have shown that it is possible to react hydrogen with toluene to produce methylcyclohexane at the electrolysis or water splitting location which can then be transported as a liquid to another location where it is dehydrogenated to hydrogen and returning liquid toluene to the original site to continue the cycle. See Niermann et al, "*Liquid Organic Hydrogen Carries (LOHC's)—Techno-Economic Analysis of LOHC's in a Defined Process Scheme*", Energy Environ. Sci. 2019, 12, 290. This development means that it is possible to separate the electrolysis location from the eventual user of the renewable hydrogen.

One reaction that has been considered for utilization of carbon dioxide is the Reverse Water Gas Shift (RWGS) reaction.

$$CO_2 + H_2 = CO + H_2O$$

This reaction converts carbon dioxide and hydrogen to carbon monoxide and water. This reaction is endothermic at room temperature and requires heat to proceed and elevated temperature and a good catalyst is required for significant carbon dioxide conversion.

Several catalysts have been disclosed for the RWGS reaction. The primary catalysts studied previously were Cu or Pt or Rh dispersed on metal oxide supports. (Daza & Kuhn, RSC Adv. 2016, 6, 49675-49691).

With the CO (Carbon Monoxide) from the RWGS reaction and hydrogen from the electrolysis of water, you have the potential for useful products through the catalyst hydrogenation of carbon monoxide to hydrocarbons. Mixtures of $H_2$ and CO are called synthesis gas or syngas. Syngas may be used as a feedstock for producing a wide range of chemical products, including liquid fuels, alcohols, acetic acid, dimethyl ether and many other chemical products. If $H_2$ from water and CO from $CO_2$ can be produced, then it is possible to truly have zero net carbon fuels and chemicals if there are no $CO_2$ or greenhouse gas emissions that are generated in the generation of the syngas and conversion of the syngas to fuels and chemicals.

The catalytic hydrogenation of CO to produce light gases, liquids, and waxes, ranging from methane to heavy hydrocarbons (C100 and higher) in addition to oxygenated hydrocarbons, is typically referred to Fischer-Tropsch (or F-T) synthesis. Traditional low temperature (<250° C.) F-T processes primarily produce a high weight (or wt. %) F-T wax (C25 and higher) from the catalytic conversion process. These F-T waxes are then hydrocracked and/or further processed to produce diesel, naphtha, and other fractions. During this hydrocracking process, light hydrocarbons are also produced, which may require additional upgrading to produce viable products. The catalysts that are commonly used for F-T are either Cobalt (Co) based, or Iron (Fe) based catalysts are also active for the water gas shift (WGS) reaction that results in the conversion of feed carbon monoxide to carbon dioxide. See more details about the state of the art in Fischer-Tropsch (S. S. Ail, S. Dasappa/Renewable and Sustainable Energy Reviews 58 (2016) 267-286).

Despite the large amount of previous work on the subject and the global importance of successfully developing these technologies, to date, good processes, systems, and catalysts to capture and convert atmospheric carbon dioxide to useful fuels and chemicals have not been developed. There is a need for better processes, systems, and catalysts.

BRIEF DESCRIPTION OF FIGURES

FIG. 5 shows the Reverse Water Gas Shift system and supporting unit operations.

FIG. 6 shows a part of an overall process flow diagram for the conversion of $H_2$ and $CO_2$ to fuels and chemicals. Specifically FIG. 6 shows the liquid fuel production system where CO and $H_2$ are reacted to produce longer chain hydrocarbons that can be used as fuel or chemicals.

SUMMARY OF INVENTION

The invention relates to a process, catalysts, materials for conversion of renewable electricity, air, and water to low or zero carbon fuels and chemicals by the direct capture of carbon dioxide from the atmosphere and the conversion of the carbon dioxide to fuels and chemicals using hydrogen produced by the electrolysis of water. The process involves conversion of water to hydrogen in an efficient electrolysis unit that uses renewable electricity as its energy source and optionally transporting the hydrogen via an LOHC system to the direct air capture (DAC) site. Hydrogen is used in a beneficial way to improve the efficiency of the DAC system. Carbon dioxide and hydrogen are reacted to carbon monoxide and water in a RWGS reactor where the heat of reaction is provided by renewable electricity. The catalyst used in the RWGS reactor is a novel solid solution catalyst. The product carbon monoxide and additional hydrogen are reacted to fuels and chemicals in a liquid fuels production reactor that uses a novel catalyst to directly produce fuels and chemicals. The net product produced is a hydrocarbon with 4 to 24 carbon atoms in length. Other products may be produced from syngas including methanol, waxes, ammonia, solvents, other fuels, and chemicals.

DETAILED DESCRIPTION OF INVENTION

Figure 1:
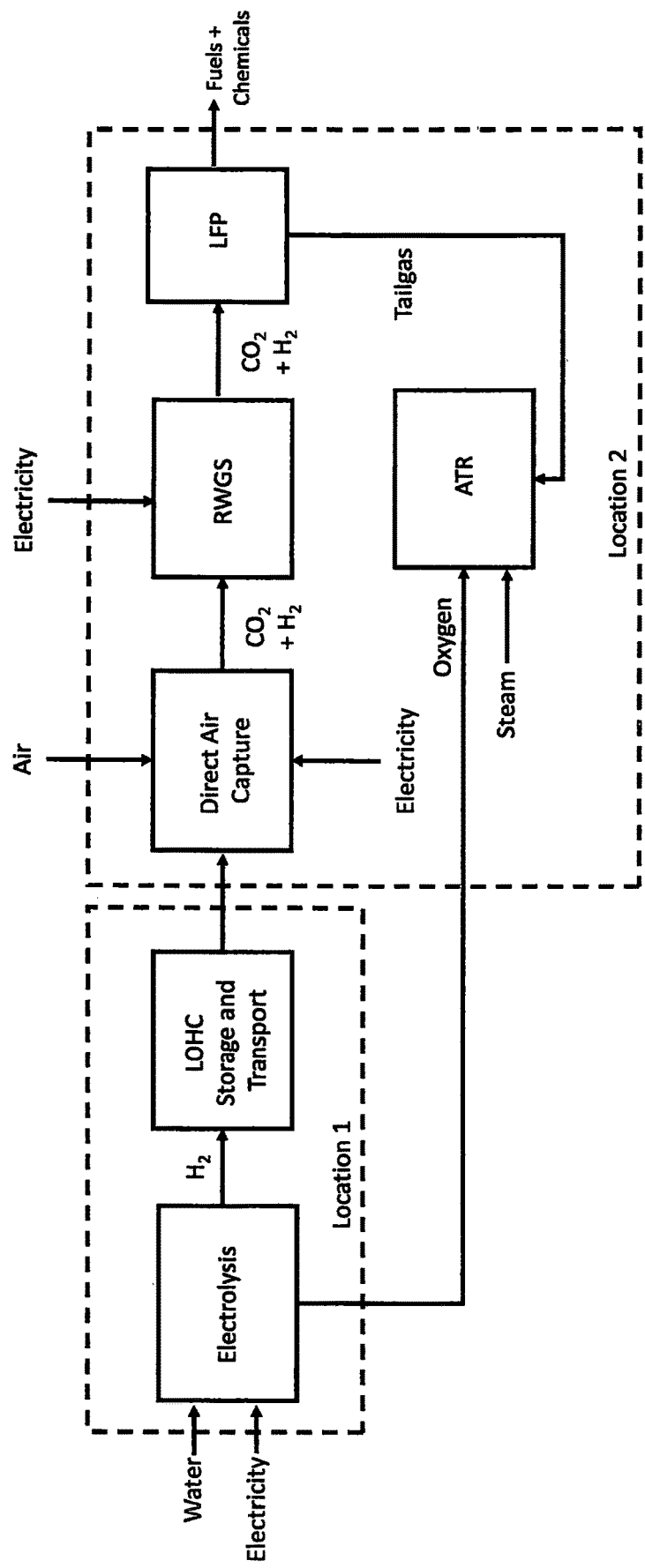
FIG. 1 shows the overall process to produce fuels and chemicals from renewable electricity, water, and air that can occur in two separate locations.

This invention involves several subsystems. FIG. 1 shows the overall process to produce fuels and chemicals from air, water, and renewable electricity. The overall process starts with the (1) production of renewable hydrogen from renewable or low carbon electricity and water via electrolysis; (2)

the renewable hydrogen can be optionally stored and transported via an Liquid Organic Hydrogen Carrier (LOHC) system to a second location; (3) Direct Air Capture (DAC) where carbon dioxide is captured from the atmosphere, hydrogen from the electrolysis step is used to improve the efficiency of the DAC process; (4) the RWGS system to produce CO from $CO_2$; (5) the Liquid Fuel Production (LFP) reactor system where syngas is converted to hydrocarbons; (6) the autothermal reformer (ATR) section that converts light hydrocarbons (C1-C5) produced in the Liquid Fuel Production (LFP) reactor to hydrogen and carbon monoxide (syngas) that is recycled back to the LFP reactor.

One other aspect of the invention is using tailgas to fire a calciner in the Direct Air Capture process. The calciner ideally would be oxygen fired, using oxygen from the electrolyzer, to concentrate the $CO_2$ from the calciner in order so it can be recycled back to the RWGS process.

From FIG. 1, the electrolysis system produces the renewable hydrogen. Water is fed to the electrolysis system. Renewable electricity is used to power the electrolysis system. Hydrogen can be produced by electrolysis of water.

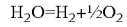

$$H_2O = H_2 + \tfrac{1}{2}O_2$$

Electrolyzers consist of an anode and a cathode separated by an electrolyte. Different electrolyzers function in slightly different ways. Different electrolyzer designs that use different electrolysis technology can be used including alkaline electrolysis, membrane electrolysis, and high temperature electrolysis. Alkaline electrolysis is preferred as it is commercially capable of the larger >1 MW scale operation. Different electrolytes can be used including liquids KOH and NaOH with or without activating compounds. Activating compounds can be added to the electrolyte to improve the stability of the electrolyte. Most ionic activators for hydrogen evolution reaction are composed of ethylenediamine-based metal chloride complexes and $Na_2MoO_4$ or $Na_2WO_4$. Different electrocatalysts can be used on the electrodes including many different combinations of metals and oxides like Raney-Nickel-Aluminum, which can be enhanced by adding cobalt or molybdenum to the alloy.

Several combinations of transition metals, such as $Pt_2Mo$, $Hf_2Fe$, and TiPt, have been used as cathode materials and have shown significantly higher electrocatalytic activity than state-of-the-art electrodes.

Some electrolyzers are designed to operate at and produce hydrogen and oxygen at elevated pressures, such as 30-50 bar. Pressurized electrolyzers are preferred as they can eliminate the energy intensive step of syngas compression. Water at the cathode combines with electrons from the external circuit to form hydrogen gas and negatively charged oxygen ions. The oxygen ions pass through the solid ceramic membrane and react at the anode to form oxygen gas and generate electrons for the external circuit. In this way, both hydrogen gas and oxygen gas are produced in the electrolyzer. In one embodiment, multiple electrolyzers are operated in parallel. No electrolyzer operates with 100% energy efficiency and energy usage is critical to the economic operation of the facility. The energy usage in the electrolyzer should be less than 200 mega-watthours (MWh)/metric ton (MT) of $H_2$ produced, and preferably less than 120 MWh/MT $H_2$ produced and more preferably less than 60 MWh/MT $H_2$ produced. For the alkaline electrolyzer embodiment, the electricity usage will be greater than 39.4 MWh/MT $H_2$ produced. However, for the high temperature electrolyzer embodiment, the electricity usage can potentially be less than 39.4 MWh/MT $H_2$ produced if waste heat is used to heat the electrolyzer above ambient temperature.

Figure 2:
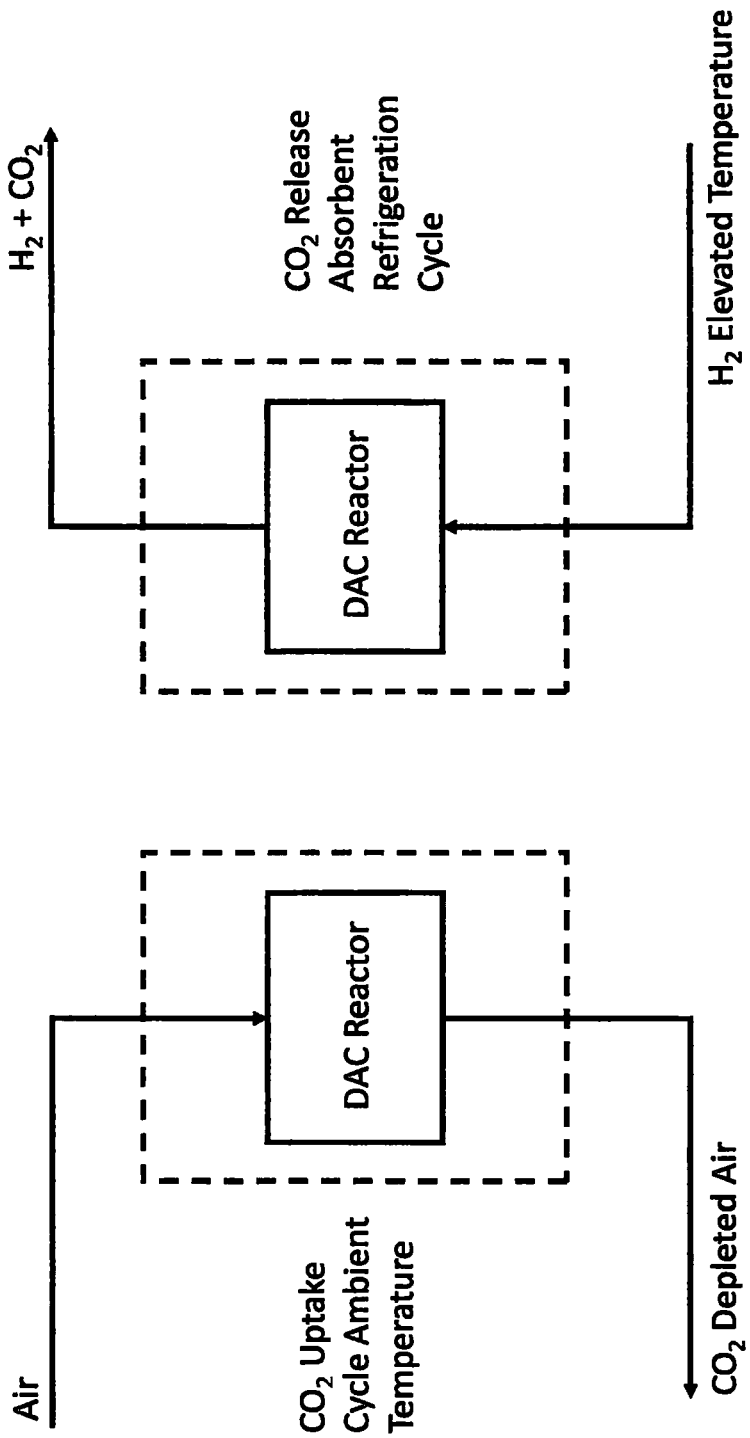
FIG. 2 shows the two cycles of direct air capture (DAC) of $CO_2$ using amine-based solid chemisorbents.

Several different Direct Air Capture (DAC) technologies can be used in the invention. The first embodiment of DAC technology is based on a solid amine-based adsorbent. FIG. 2 shows one embodiment of the invention. A supported amine adsorbent based on primary, secondary, or tertiary amines is loaded into the DAC reactor. The amine adsorbent is capable of chemisorbing carbon dioxide in the air that passes through the DAC reactor. This results in a carbon dioxide depleted air stream leaving the DAC reactor. This occurs at near ambient temperatures and pressures. A blower can be used to draw the air through the reactor. Pressure drop through the DAC reactor is optimized by the loading of the solid amine adsorbent into the DAC reactor and by managing the size of the amine adsorbent.

There are at least three classes of solid supported amine adsorbents that can be used. Class 1 adsorbents are composed of polymeric or oxides support (typically silica) that are physically loaded with amine containing small molecules or polymers. Class 2 adsorbents are based on amine species that are covalently bound to the surface of the solid support such as via the use of organosilanes. For example, a class 1 adsorbents would be tetraethlyenepantamine or diethanolamine impregnated on MCM-41 silica. A typical class 2 adsorbent is triamine-grafted pore-expanded MCM-41 has shown good adsorption at low carbon dioxide partial pressure. Class 3 adsorbents are amine-based solid adsorbents described as hyperbranched aminosilica (HAS) materials which are synthesized via in situ ring opening polymerization of aziridine off porous supports. These adsorbents typically have amine loadings of 2-10 mmol/g; pore diameters of 4 to 7 nm; BET surface areas of 40-600 $m^2/g$; and pore volumes of 0.1-0.8 cc/g. These materials work well with humid or dry air at ambient conditions and have shown carbon dioxide adsorption of 0.5-4.0 mmol/g at carbon dioxide concentrations of approximately 400 ppm. Ideally, the DAC reactor is operated in such a way that approximately 20-50% of the carbon dioxide in the air passing through the DAC reactor is removed. Removal of more than 50% of carbon dioxide is generally not favored as the ability of the adsorbent to capture the carbon dioxide is significantly reduced. After the $CO_2$ uptake cycle is complete, the DAC reactor is switched to the $CO_2$ release adsorbent regeneration cycle. In this cycle, hydrogen that was produced in the electrolyzer is heated to approximately 90-120° C. through indirect heat exchange. The hydrogen is passed through the DAC reactor where the adsorbed carbon dioxide is released and mixes with the carbon dioxide gas. Typically, the amount of hydrogen gas used results in a hydrogen to carbon dioxide molar ratio in the gas leaving the DAC reactor to be 2.0 and 3.0 mol/mol. This stream becomes the RWGS feed stream in FIG. 5. This integration specifically improves the efficiency of the DAC system as no steam is needed and no separation is required.

Figure 3:
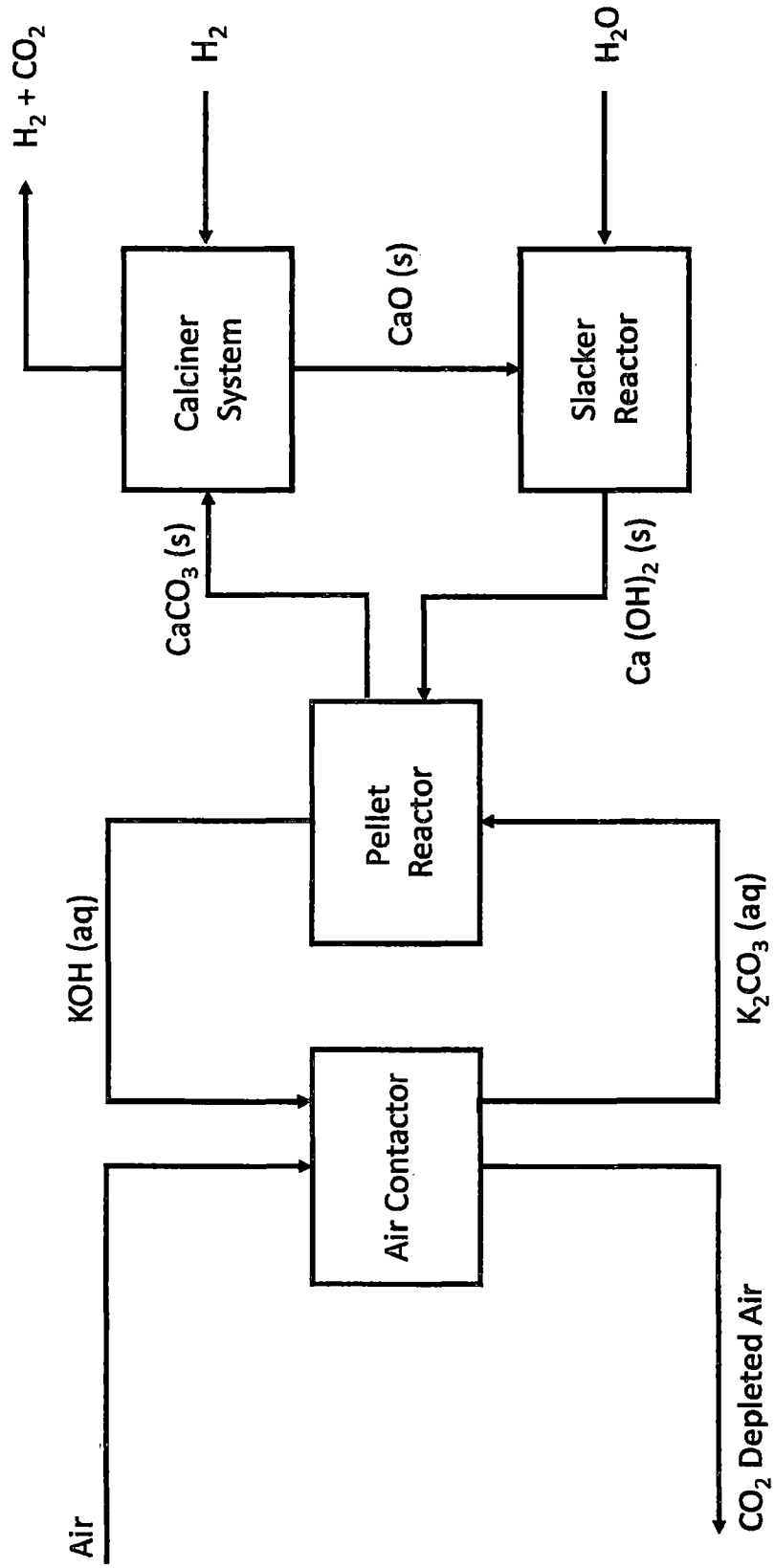
FIG. 3 shows the direct air capture (DAC) of $CO_2$ using metal hydroxides/carbonate cycles.

The second embodiment of the DAC technology is based on a different process chemistry. FIG. 3 shows the embodiment. This process involves the capture of carbon dioxide from the air via metal hydroxide conversion to a metal carbonate. Air is passed through an air contactor with the use of a blower. The Air Contactor contacts the carbon dioxide laden air with aqueous KOH. The KOH reacts with the carbon dioxide to produce aqueous $K_2CO_3$. The aqueous $K_2CO_3$ is reacted with solid $Ca(OH)_2$ in a pellet reactor. The $K_2CO_3$ coverts back to KOH while the $Ca(OH)_2$ is converted to solid $CaCO_3$. The calcium carbonate is fed to a Calciner System where the calcium carbonate is converted to CaO. The calciner system is novel as a circulating fluid bed that operates at 50 psig or higher. It is an oxygen blown circulating fluid bed system. The oxygen is used as a fluidization gas at a superficial velocity between 0.25 to 2.5 m/s. Natural gas or other combustible containing gas is fed into the bed of solids though lances where the oxygen and gas react to raise the temperature to 900 C. This causes the reaction of the $CaCO_3$ to $CaO+CO_2$ with over 90% conversion efficiency. The solid CaO is separated from the gaseous $CO_2$ in a cyclone system. The solid CaO is fed to the Slaker reactor where it is converted $Ca(OH)_2$ to be used in the pellet reactor. The hot $CO_2$ containing gas is immediately mixed with hydrogen that was produced in the electrolyzer. Typically, the amount of hydrogen gas mixed with the carbon dioxide results in a hydrogen to carbon dioxide molar ratio in the gas leaving the DAC reactor system to be 2.0 and 3.0 mol/mol. This stream becomes the RWGS feed stream in FIG. 5. This integration specifically improves the efficiency of the DAC system as no cooling or compression of the carbon dioxide is required. The heating requirement in this embodiment is also significantly reduced for the RWGS feed as the mixed gas is already over 300° C. or even higher.

Figure 4:
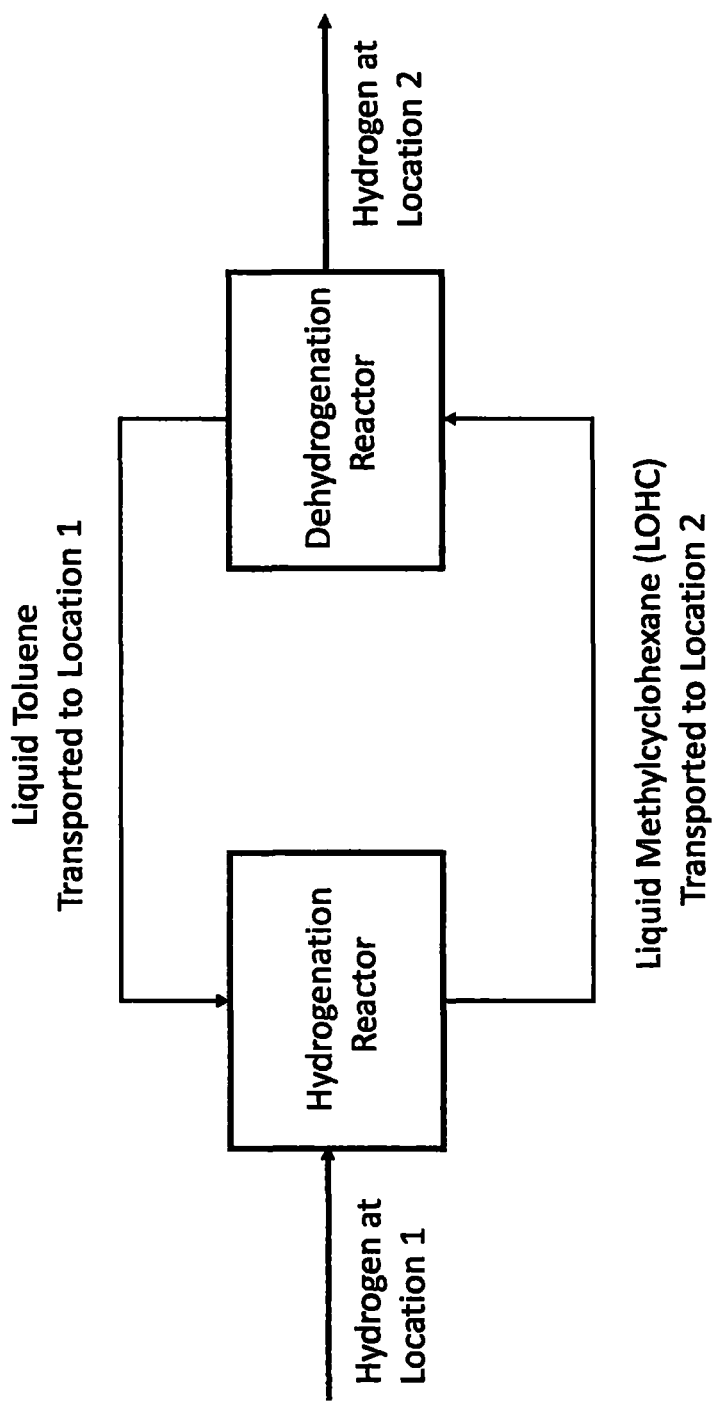
FIG. 4 shows the LOHC process for transporting hydrogen gas produced at Location 1 to Location 2.

FIG. 4 shows the LOHC system in one embodiment of the invention. It is possible that the electrolyzer and the DAC system are in the same physical location. However, it seems possible that the DAC unit would be at the source of consumption of the product fuels and chemicals while the electrolyzer may be in a region where ample sunlight, wind or other renewable or low carbon resource that can be used to generate renewable electricity to produce the hydrogen. In this case, the hydrogen produced by the electrolyzer would be required to be transported to the second location. FIG. 4 shows how this can be done using an LOHC system. Although several different LOHC materials are possible, the most promising appears to be methylcyclohexane (MHC) that can be produced by the reaction of toluene with hydrogen. This is done in the hydrogenation reactor of FIG. 4. MHC is a liquid that can easily be transported to Location 2 that is different from the electrolyzer location. The MHC can then be dehydrogenated at Location 2 to produce hydrogen gas and toluene. The toluene is then transported back to Location 1 to complete the cycle. The dehydrogenation is a catalytic reactor system. Numerous catalysts can be used but can include S-Pt on Alumina. The dehydrogenation reaction temperature is between 340-360° C. with a pressure between 1-30 bar. The MCH conversion is greater than 95% and the hydrogen yield is greater than 95%. The high temperature of the dehydrogenation reactor can be use beneficially metal hydroxide DAC process. The hydrogen produced via the dehydrogenation reactor can be mixed with the $CO_2$ produced by the calciner and result in a gas stream with a temperature above 400-500° C. that can be used as immediate (with some additional preheat) feed to the RWGS reactor system shown in FIG. 5.

Figure 5:
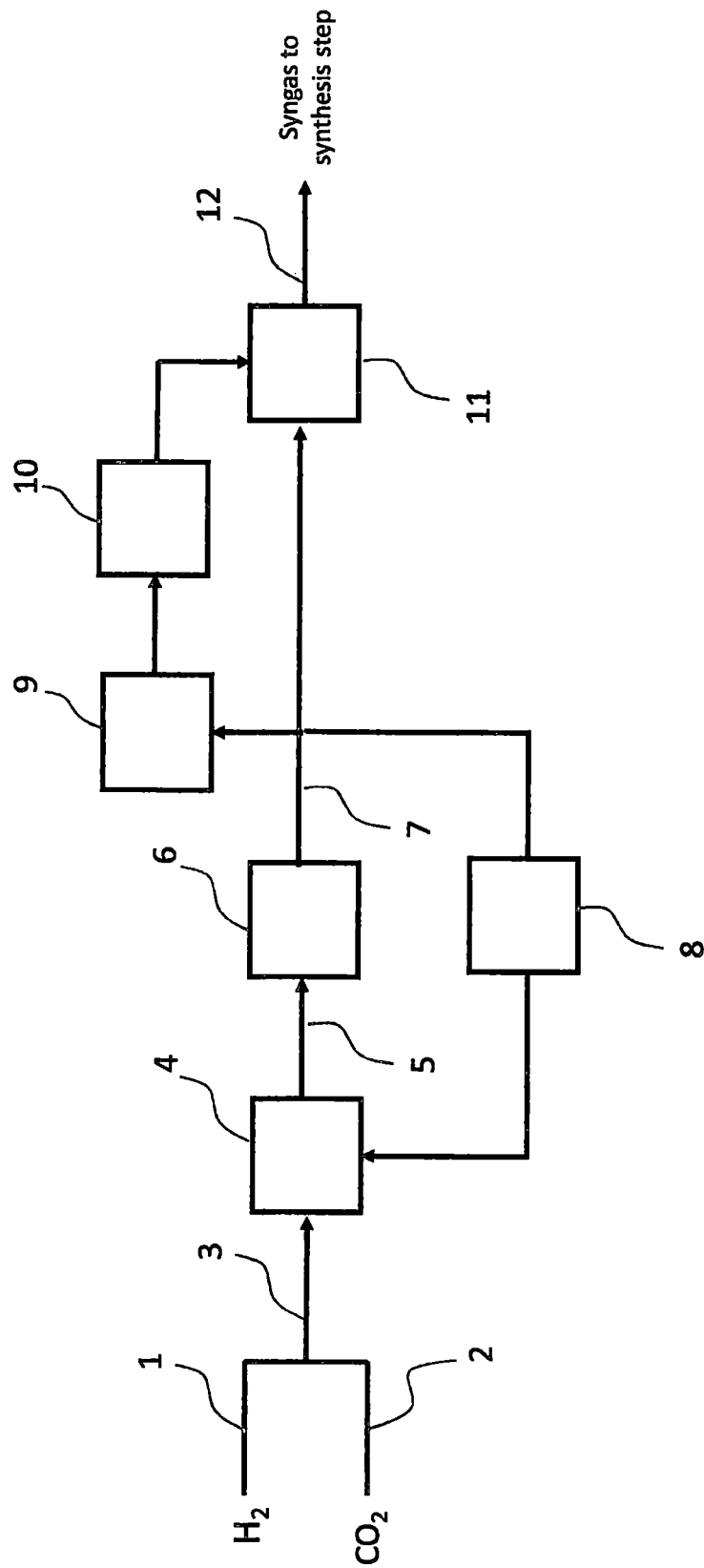
FIGS. 5 and 6 show an integrated high efficiency process for the conversion of carbon dioxide, water, and renewable electricity into renewable fuels and chemicals.

FIG. 5 shows the RWGS system to produce CO from $CO_2$. Zero carbon or ultra-low carbon fuels and chemicals require that fossil fuels are not combusted in the process of producing the fuels and chemicals. This means that any heating of the feeds to the integrated process needs to be by indirect means (cross exchangers) or via electric heating where the electricity comes from a zero carbon or renewable source such as wind, solar, geothermal, or nuclear.

Hydrogen and carbon dioxide are in streams 1 and 2 in FIG. 5 forming a mixed gas (stream 3). The ratio of $H_2/CO_2$ is between 2.0-5.0 mol/mol, more preferably between 3.0-4.0 mol/mol. The mixed RWGS feedstock can be heated by indirect heat exchange to a temperature of greater than 900° F. in unit 4. It is important that this initial temperature rise is done without the use of direct combustion of a carbon containing gas to provide the heat as that would mean that $CO_2$ was being produced and could possibly negate the impact of converting $CO_2$ to useful fuels and chemicals.

The RWGS feed gas comprising a mixture of $H_2$ and $CO_2$ is heated to an inlet temperature greater than 1400° F. (stream 5), or preferably greater than 1500° F., at least partially in a preheater outside the main reactor vessel to produce a heated feed gas.

FIG. 5 shows the preheater as unit 4 which is electrically heated and raises the temperature of the feed gas through indirect heat exchange to greater than 1400° F., preferably greater than 1500° F., and more preferably greater than 1600° F. There are numerous ways that the electrical heating of the feed gas can be done. One way is through electrical heating in an electrically heated radiant furnace. In this embodiment, at least a portion of the feed gas passes through a heating coil in a furnace. In the furnace, the heating coil is surrounded by radiant electric heating elements. The radiant electric heating elements can be made from numerous materials. The heating elements may be nickel chromium alloys. These elements may be in rolled strips or wires or cast as zig zag patterns. The elements are backed by an insulated steel shell and ceramic fiber is generally used for insulation. The radiant elements may be divided into zones to give a controlled pattern of heating. Multiple coils and multiple zones may be needed to provide the heat to the feed gas and produce a heated feed gas. Radiant furnaces require proper design of the heating elements and fluid coils to ensure good view factors and good heat transfer. In another embodiment of the invention, the gas is passed directly over heating elements whereby the gas is heated by convective heat transfer. The electricity usage by the radiant furnace should be as low as possible. The electricity usage by the radiant furnace is less than 0.5 MWh (megawatt-hour) electricity/metric ton (MT) of $CO_2$ in the feed gas; more preferably less than 0.40 MWh/MT $CO_2$; and even more preferably less than 0.20 MWh/MT $CO_2$.

The heated RWGS feed gas then is fed into the main RWGS reactor vessel (unit 6). There are two possible embodiments of the main RWGS reactor vessel. In the first embodiment, the main RWGS reactor vessel is adiabatic or nearly adiabatic and is designed to minimize heat loss, but no added heat is added to the main reactor vessel and the temperature in the main reactor vessel will decline from the inlet to the outlet of the reactor. In the second embodiment, the main RWGS reactor vessel is similarly designed but additional heat is added to the vessel to maintain an isothermal or nearly isothermal temperature profile in the vessel. Heat may be added to the vessel by internal or external heaters or by other means.

The main RWGS reactor vessel (unit 6) is a reactor with a length longer than diameter. The entrance to the main reactor vessel is smaller than the overall diameter of the vessel. The main reactor vessel is a steel vessel. The steel vessel is insulated internally to limit heat loss. Various insulations including poured or castable refractory lining or insulating bricks may be used to limit the heat losses to the environment. (See Harbison-Walker Handbook of Refractory Practices, 2005, https://mha-net.org/docs/Harbison%20Walker%202005%20Handbook.pdf)

A bed of catalyst is inside the main reactor vessel. The catalyst can be in the form of granules, pellets, spheres, trilobes, quadra-lobes, monoliths, or any other engineered shape to minimize pressure drop across the reactor. Ideally the shape and particle size of the catalyst particles is managed such that pressure drop across the reactor is less than 50 pounds per square inch (psi) [345 kPa] and more preferably less than 20 psi [138 kPa]. The size of the catalyst form can have a characteristic dimension of between 1 mm to 10 mm or larger. The catalyst particle is a structured material that is porous material with an internal surface area greater than 40 m$^2$/g, more preferably greater than 80 m$^2$/g with a preferred surface area of 100 m$^2$/g. Several catalyst materials are possible that can catalyze the RWGS reaction. RWGS catalysts that have been studied previously were Cu or Pt or Rh dispersed on metal oxide supports. (Daza & Kuhn, *RSC Adv.* 2016, 6, 49675-49691). We have found that the preferred catalyst is a solid solution catalyst with a transition metal on a metal oxide support.

The RWGS catalyst used in the process is a high-performance solid solution-based catalyst that is highly versatile, and which efficiently performs the RWGS reaction. The robust, solid solution catalyst has high thermal stability up to 1,100° C., it does not form carbon (coking), and has good resistance to contaminants that may be present in captured $CO_2$ streams.

This catalyst exhibits high activity at low metal concentrations (0.5-20 wt. %), compared to other catalysts that require at least 30 wt. % transition or other metal loadings. Furthermore, the use of expensive precious metals to enhance catalyst performance is not necessary. The manufacturing process for the RWGS catalyst is important as well in that it produces a catalyst that forms a unique solid solution phase, bi-metallic crystalline phase that leads to no segregation of the metal phases. This unique chemical structure leads to enhanced resistance to coking, when compared to conventional metal supported catalysts. This also leads to enhanced resistance to poisons such as sulfur and ammonia. In addition, this catalyst has enhanced catalytic activity at lower surface area compared to monometallic segregated catalyst phase. This catalyst requires no alkali promotion needed to curb the carbon deposition.

The per pass conversion of $CO_2$ to CO in the main RWGS reactor vessel is generally 60-90% and more preferably 70-90%. If the embodiment of an adiabatic reactor is used, the temperature in the main RWGS reactor vessel will decline from the inlet to the outlet. The main RWGS reactor vessel outlet temperature is 100-200° F. less than the main reactor vessel inlet temperature and more preferably between 105 and 160° F. lower than the main reactor inlet temperature. The RWGS Weight Hourly Space Velocity (WHSV) which is the mass flow rate of RWGS reactants ($H_2+CO_2$) per hour divided by the mass of the catalyst in the main RWGS reactor bed is between 1,000 hr$^{-1}$ and 60,000 hr$^{-1}$ and more preferably between 5,000 hr$^{-1}$ and 30,000 hr$^{-1}$.

The gas leaving the main RWGS reactor vessel is the RWGS product gas (stream 7). The RWGS product gas comprises carbon monoxide (CO), hydrogen ($H_2$), unreacted carbon dioxide ($CO_2$), water ($H_2O$). Additionally, the RWGS product gas may also comprise a small amount of methane ($CH_4$) that was produced in the main reactor vessel by a side reaction.

The RWGS product gas can be used in a variety of ways at this point in the process. The product gas can be cooled and compressed and used in downstream process to produce fuels and chemicals. The RWGS product gas can also be cooled, compressed (in unit 8) and sent back to the preheater and fed back to the main reactor vessel.

The RWGS product gas can also be reheated in second electric preheater and sent to a second reactor vessel where additional conversion of $CO_2$ to CO can occur as shown in units 9 and 10. Unit 11 shows optional compression before the syngas is sent to the Liquid Fuel Production synthesis step.

Figure 6:
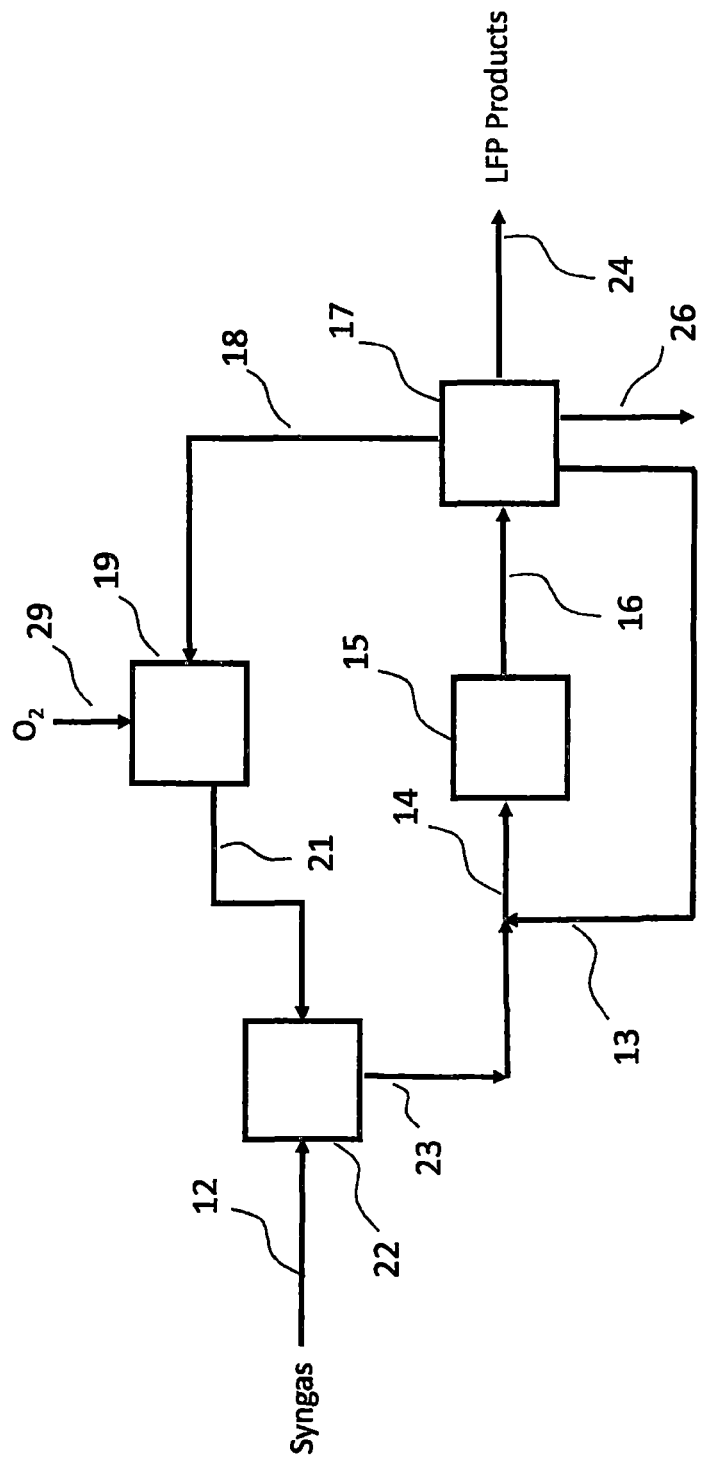

FIG. 6 shows the Liquid Fuels Production (LFP) reactor system. This is also known as the hydrocarbon synthesis step. The LFP reactor converts CO and $H_2$ into long chain hydrocarbons that can be used as liquid fuels and chemicals. Syngas (stream 12) is blended with recycled syngas to produce an LFP reactor feed stream 13 and optionally the products (stream 21) from the ATR (unit 19) as described below. The blended gases feeding to the LFP reactor are shown as stream 14. The LFP reactor feed comprises $H_2$ and CO. Ideally the $H_2$ to CO ratio in the stream is between 1.9 and 2.2 mol/mol.

The LFP reactor (unit 15) is a multi-tubular fixed bed reactor system. Each LFP reactor tube can be between 13 mm and 26 mm in diameter. The length of the reactor tube is generally greater than 6 meters in length and more preferably greater than 10 meters in length. The LFP reactors are generally vertically oriented with LFP reactor feed entering at the top of the LFP reactor. However, horizontal reactor orientation is possible in some circumstances and setting the reactor at an angle may also be advantageous in some circumstances where there are height limitations.

Most of the length of the LFP reactor tube is filled with LFP catalyst. The LFP catalyst may also be blended with diluent such as silica or alumina to aid in the distribution of the LFP reactor feed into and through the LFP reactor tube. The chemical reaction that takes place in the LFP reactor produces an LFP product gas comprising hydrocarbon products from four to twenty-four carbons in length ($C_4$-$C_{24}$ hydrocarbons) as well as water. It is important that the LFP reactor not produce any significant amount of $CO_2$. Less than 2% of the CO in the LFP reactor feed should be converted to $CO_2$ in the LFP reactor. It is also important that only a limited amount of the carbon monoxide in the LFP reactor feed be converted to hydrocarbons with a carbon number greater than 24. Less than 10 wgt % of the hydrocarbon fraction of the LFP product should have a carbon number greater than 24. More preferably, less than 4 wgt % of the hydrocarbon fraction of the LFP product should have a carbon number greater than 24.

As discussed above, Fischer-Tropsch (F-T) processes generally make hydrocarbon products that are from 1 to 100 carbon atoms in length with a majority in the wax range (C24+). The LFP catalyst used in an embodiment of this invention, however, does not produce heavy hydrocarbons with the same yield as other catalysts used in traditional F-T processes.

In some embodiments of the invention, the LFP catalyst has insignificant activity for the conversion of conversion of CO to $CO_2$ via the water-gas-shift reaction. In some embodiments of the invention, the water gas shift conversion of CO to $CO_2$ is less than 5% of the CO in the feed. In some embodiments, the LFP catalyst comprises nickel as the active metal. In some embodiments, the LFP catalyst comprises cobalt as the active metal. In some embodiments, the LFP catalyst comprises cobalt and nickel as the active metal. The LFP catalyst is supported on a metal oxide support that chosen from a group of alumina, silica, titania, activated carbon, carbon nanotubes, zeolites or other support materials with sufficient size, shape, pore diameter, surface area, crush strength, effective pellet radius, or mixtures thereof.

The catalyst can have various shapes of various lobed supports with either three, four, or five lobes with two or more of the lobes being longer than the other two shorter lobes, with both the longer lobes being symmetric. The distance from the mid-point of the support or the mid-point of each lobe is called the effective pellet radius which is an important parameter to achieve the desired selectivity to the $C_4$ to $C_{24}$ hydrocarbons. The LFP catalyst promoters may include one of the following: cerium, ruthenium, lanthanum, platinum, rhenium, gold, nickel, or rhodium. The LFP catalyst promoters are less than 1 wgt % of the total catalyst and preferably less than 0.5 wgt % and even more preferably less than 0.1 wt. %.

The LFP catalyst support has a pore diameter greater than 8 nanometers (nm), a mean effective pellet radius of less than 60 micrometers (urn) a crush strength greater than 3 lbs/mm and a BET surface area of greater than 125 m²/g. The catalyst after metal impregnation has a metal dispersion of about 4%. Several types of supports have been found to maximize the $C_4$-$C_{24}$ hydrocarbon yield. These include alumina, alumina/silica combinations, activated carbon, carbon nanotubes, and/or zeolite-based supports.

The LFP fixed bed reactor is operated in a manner to maximize the $C_4$-$C_{24}$ hydrocarbon yield.

Alternatively, the LFP fixed bed reactor uses a traditional F-T catalyst that produces mostly wax. The LFP reactor in one embodiment is operated at pressures between 150 to 450 psi. The reactor is operated over a temperature range from 350° F. to 460° F. and more typically at around 410° F. The F-T reaction is exothermic. The temperature of the reactor is maintained inside the LFP reactor tubes by the reactor tube bundle being placed into a heat exchanger where boiling steam is present on the outside of the LFP reactor tubes. The steam temperature is at a lower temperature than the LFP reaction temperature so that heat flows from the LFP reactor tube to the lower temperature steam. The steam temperature is maintained by maintaining the pressure of the steam. The steam is generally saturated steam.

The CO conversion in the LFP reactor is maintained at between 30 to 80 mole % CO conversion per pass. CO can be recycled for extra conversion or sent to a downstream additional LFP reactor. The carbon selectivity to $CO_2$ is minimized to less than 4% of the converted CO and more preferably less than 1%. The carbon selectivity to C4-C24 hydrocarbons is between 60 and 90%. The LFP reactor product gas contains the desired C4-C24 hydrocarbons as well as unreacted carbon monoxide, hydrogen, water, a small amount of C1-C5 hydrocarbons and a small amount of C24+ hydrocarbons. The desired product is separated from the stream by distillation or any other acceptable means. The carbon selectivity is defined as:

$$C4 - C24 \text{ Carbon Selectivity} = \frac{1}{n_{CO\,Converted}} \sum_{i=4}^{24} in_i$$

Where $n_{co}$ Converted is the molar flowrate of CO that was converted in the LFP reactor; $n_i$ is the molar flowrate of $i^{th}$ carbon numbered hydrocarbon that was created in the LFP reactor. The carbon selectivity to carbon dioxide is defined as $$CO_2 \text{ Carbon Selectivity} = \frac{1}{n_{CO\,Converted}} n_{CO_2}$$

Where $n_{co2}$ is the molar flowrate of $CO_2$ that was created in the LFP reactor. This is highly desirable for the zero carbon fuels and chemical production process that starts with carbon dioxide as a feedstock.

The products proceed from the bottom of the reactor. There is the possibility that heavy hydrocarbons (C24+) are produced so the reactor exit can remove those products. If the LFP reactor is operated at the right conditions with the catalyst, there will be little or no heavy hydrocarbons. The primary LFP products are stream 16 which are cooled condensed in unit 17. The unreacted carbon monoxide, hydrogen, and C1-C5 hydrocarbons or tailgas (unit 18) are part of the feed to the Auto-thermal Reformer. FIG. 6 also shows the auto-thermal reformer (ATR) (unit 19) section of the process. In the Auto-thermal Reformer (ATR), the ATR hydrocarbon feed comprises carbon monoxide, hydrogen, and C1-C5 hydrocarbons. The Auto-thermal reforming of natural gas that is predominately methane (C1) to carbon monoxide and hydrogen has been commercially practiced for many years. See K. Aasberg-Petersen et al./Journal of Natural Gas Science and Engineering 3 (2011) 423-459.

The ATR used in this invention is not necessarily conventional in that the desire is to produce a product that is high in CO, where the product $H_2$ to CO ratio is between 1.9 to 2.2 mol/mol, and the $CO_2$ in the product gas is less than 10 mol %. The ATR oxidant feed comprises steam and 02 where the 02 is at least partially produced by the electrolysis of $H_2O$ (stream 29). The ATR oxidant feed and the ATR hydrocarbon feed are preheated and then reacted in an ATR burner where the oxidant and the hydrocarbon are partially oxidized at temperatures in the range of 950-1,050° C. The ATR reactor can be divided into three zones; the combustion zone (or burner) where at least portion of the ATR hydrocarbon feedstock is fully combusted to $H_2O$ and $CO_2$.

In the thermal zone further conversion occurs by homogeneous gas-phase-reactions. These reactions are slower reactions than the combustion reactions like CO oxidation and pyrolysis reactions involving higher hydrocarbons. The main overall reactions in the thermal zone are the homogeneous gas-phase steam hydrocarbon reforming and the shift reaction. In the catalytic zone, the final conversion of hydrocarbons takes place through heterogeneous catalytic reactions including steam methane reforming and water gas shift reaction. The resulting ATR product gas has a composition that is close to the predicted thermodynamic equilibrium composition. The actual ATR product gas composition is the same as the thermodynamic equilibrium composition within a difference of less than 70° C. This is the so-called equilibrium approach temperature.

To keep the amount of $CO_2$ produced in the ATR to a minimum, the amount of steam in the ATR oxidant feed needs to be kept as low as possible that still results in a low soot ATR product gas that is close to the equilibrium predicted composition. Typically, the total steam to carbon ratio (mol/mol) in the combined ATR feed (oxidant+hydrocarbon) should be between 0.4 to 1.0, with the optimum being around 0.6.

The ATR product leaves the ATR catalytic zone at temperatures more than 800° C. The ATR product is cooled to lower temperatures through a waste heat boiler (unit 22) where the heat is transferred to generate steam. This steam, as well as the lower pressure steam produced by the LFP reactor, can be used to generate electricity.

Suitable ATR catalysts for the catalytic zone reactions are typically nickel based. The RWGS catalyst can be used as an ATR catalyst. Other suitable ATR catalysts are nickel on alpha phase alumina, or magnesium alumina spinel ($MgAl_2O_4$), which are used with or without precious metal promoters where the precious metal promoter comprises gold, platinum, rhenium, or ruthenium. Spinels have a higher melting point higher thermal strength and stability than alumina-based catalysts.

The ATR product can be blended with the RWGS product and be used as LFP reactor feed. This results in a high utilization of the original $CO_2$ to C4 to C24 hydrocarbon products.

In some embodiments, the LFP product gas is not suitable as a direct feed to the ATR and must be pre-reformed. In those cases, the LFP product gas comprising the unreacted carbon monoxide, hydrogen, and C1-C5 hydrocarbons comprise the pre-reformer hydrocarbon feed gas. Generally, the higher hydrocarbons and carbon oxides in the stream require the use of a pre-reformer instead of directly being used in as ATR hydrocarbon feed. The pre-reformer is generally an adiabatic reactor. The adiabatic pre-reformer converts higher hydrocarbons in the pre-reformer feed into a mixture of methane, steam, carbon oxides and hydrogen that are then suitable as ATR hydrocarbon feed. One benefit of using a pre-reformer is that it enables higher ATR hydrocarbon feed pre-heating that can reduce the oxygen used in the ATR. The resulting integrated process as described above results in high conversion of carbon dioxide to C4-C24 hydrocarbon products (stream 24) that are suitable as fuels or chemicals.

The invention claimed is:

1. An integrated process for the conversion of feed streams comprising air, electricity, and water to a product stream comprising hydrocarbons, the process comprising:
   a. an electrolysis step where an electrolyzer feed stream comprising water is converted to an electrolyzer product stream comprising hydrogen and oxygen where at least a portion of the electricity used in the electrolysis step is from renewable sources;
   b. a carbon dioxide step, where carbon dioxide is obtained;
   c. a reverse water gas shift step where at least a portion of the hydrogen from the electrolyzer product stream is mixed with carbon dioxide from the carbon dioxide step to produce a mixture, where the mixture is heated without use of direct combustion of a carbon-containing gas, and where the carbon dioxide and hydrogen are reacted to produce a reverse water gas shift product stream comprising carbon monoxide;
   d. a hydrocarbon synthesis step where at least a portion of the hydrogen from the electrolyzer product stream is reacted with a stream comprising at least a portion of the reverse water gas shift product stream to produce a hydrocarbon synthesis product stream, and where a portion of the carbon monoxide of the reverse water gas shift product stream is converted to carbon dioxide, and where less than 5 percent of the carbon monoxide is converted to carbon dioxide;
   e. an autothermal reforming step where at least a portion of the oxygen produced by electrolysis is reacted with a stream or streams comprising unreacted reactants from the hydrocarbon synthesis step, where the autothermal reforming step provides a product comprising hydrogen, carbon monoxide and carbon dioxide, and wherein the ratio of hydrogen to carbon monoxide is between 1.9 mol/mol and 2.2 mol/mol, and wherein the carbon dioxide in the product is less than 10 mol %.

2. The integrated process of claim 1 wherein the electrolysis step uses an electrocatalyst used on the electrodes in the electrolyzer wherein the electrocatalyst comprises an ethylenediamine-based metal chloride complex.

3. The integrated process of claim 2 wherein the electrocatalyst further comprises Na2MoO4.

4. The integrated process of claim 2 wherein the electrocatalyst further comprises Na2WO4.

5. The integrated process of claim 2 wherein the electrocatalyst further comprises a combination of a metal and Raney-Nickel-Aluminum.

6. The integrated process of claim 5 wherein the electrocatalyst further comprises cobalt in the alloy.

7. The integrated process of claim 5 wherein the electrocatalyst further comprises molybdenum in the alloy.

8. The integrated process of claim 1 where the reverse water gas shift reactor vessel is adiabatic and is designed to minimize heat loss, wherein no heat is added to the main reactor vessel and the temperature in the main reactor vessel declines from the inlet to the outlet of the reactor.

9. The integrated process of claim 1 where the reverse water gas shift reactor vessel is adiabatic and is designed to minimize heat loss, wherein heat is added to the vessel to maintain an isothermal temperature profile in the vessel.

10. The integrated process of claim 1 wherein the catalyst used inside the main reverse water gas shift reactor vessel is a solid solution catalyst with a transition metal on a metal oxide support.

11. The integrated process of claim 1 with an auto-thermal reforming step where at least a portion of the oxygen produced by electrolysis is reacted with a stream or streams comprising unreacted reactants from the hydrocarbon synthesis step.

12. The integrated process of claim 1, where the autothermal reforming step is performed in an autothermal reforming reactor, and where the autothermal reforming reactor has three zones, and where the hydrocarbon synthesis step is performed in an liquid fuels production reactor, and where the liquid fuels production reactor is a multi-tubular fixed bed reactor system, and wherein each liquid fuels production reactor in the multi-tubular fixed bed reactor system is between 13 mm and 26 mm diameter.

* * * * *